United States Patent [19]
Kwak

[11] Patent Number: 5,741,400
[45] Date of Patent: Apr. 21, 1998

[54] METHOD FOR MANUFACTURING A MUGWORT IMPREGNATED PAD

[76] Inventor: Chang Keun Kwak, 1129, Jegi-Dong, Dongdaemun-Ku, Seoul, Rep. of Korea

[21] Appl. No.: 684,545

[22] Filed: Jul. 19, 1996

[30] Foreign Application Priority Data

Mar. 12, 1996 [KR] Rep. of Korea ............... 96-6431

[51] Int. Cl.[6] ............................................. D21H 17/21
[52] U.S. Cl. .................... 162/158; 162/184; 424/413; 424/443; 424/446
[58] Field of Search ............................. 424/76.9, 413, 424/443, 445, 446, 447, 449; 604/358, 359, 367, 374, 375; 162/20, 91, 99, 158, 163, 184

[56] References Cited

U.S. PATENT DOCUMENTS

| | | |
|---|---|---|
| 4,657,531 | 4/1987 | Choi .................................. 604/23 |
| 5,146,633 | 9/1992 | Kim et al. ............................ 5/421 |
| 5,468,493 | 11/1995 | Funkunaga ...................... 424/195.1 |

*Primary Examiner*—Donald E. Czaja
*Assistant Examiner*—Steven B. Leavitt
*Attorney, Agent, or Firm*—Snell & Wilmer

[57] ABSTRACT

Disclosed is a pad including a face on which liquid mugwort or powder mugwort is spread or impregnated and a pad including more than one sheet of mugwort-impregnated paper. A method for making a mugwort-impregnated pad, including the steps of: crushing a lump of dry mugwort into 50–200 mesh size pieces; straining the crushed mugwort to obtain mugwort naps without a stalk and chlorophyll; fumigating the mugwort naps at a temperature of about 80°–130° for 1 or 2 hours; diffusing the fumigated mugwort naps in water; providing diffused mugwort naps to a refiner and mixing the naps with a lump of dissociated pulp; preparing a sheet of paper by dehydrating the mixture and paper process; and attaching more than one sheet of paper on a pad.

13 Claims, 5 Drawing Sheets

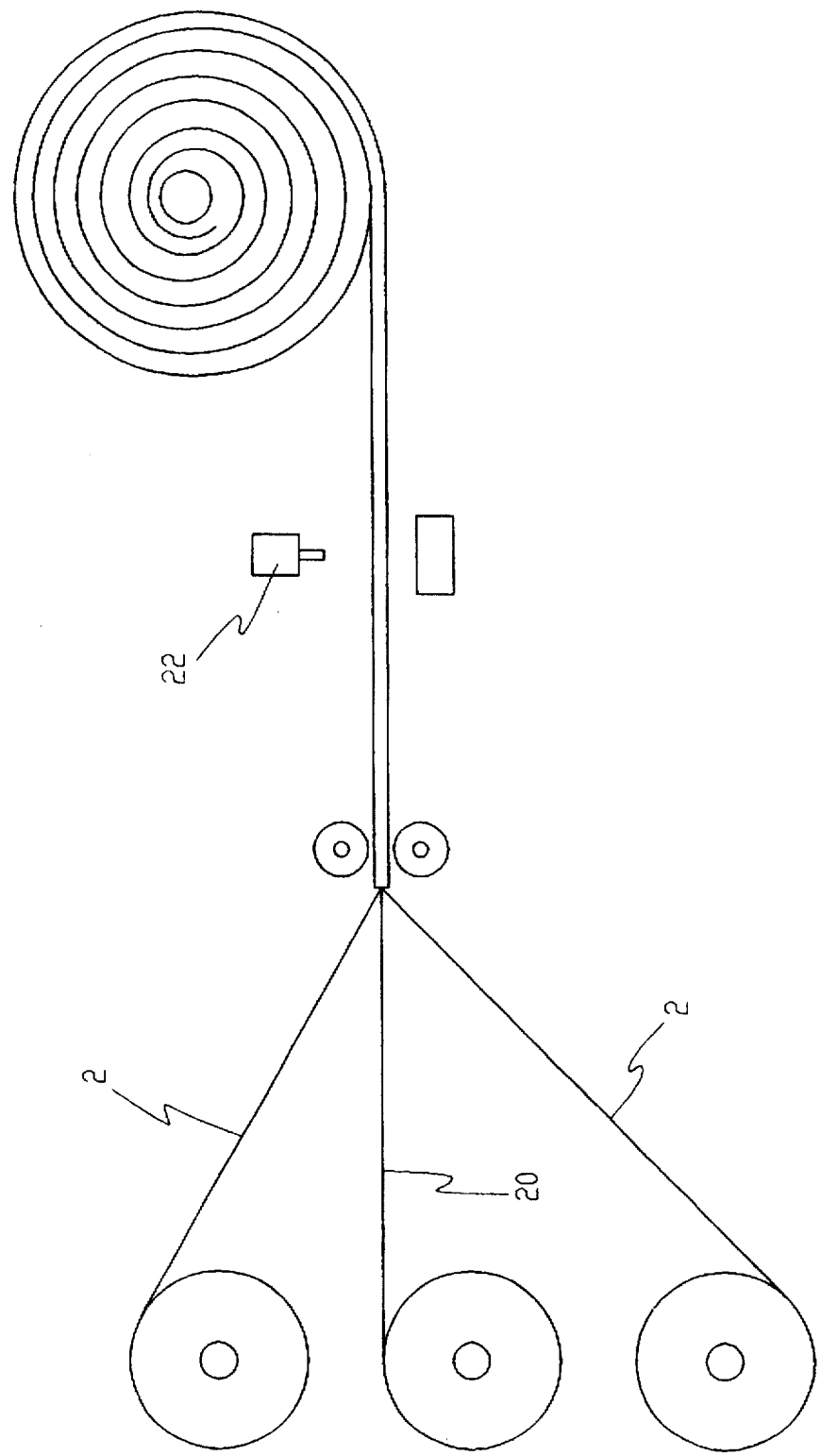

5,741,400

METHOD FOR MANUFACTURING A MUGWORT IMPREGNATED PAD

BACKGROUND OF THE INVENTION

1. Field of the Invention

The present invention relates to a pad and a method for manufacturing the same and, more particularly, to a mugwort-impregnated pad which is suitable to a hygienic band, and a method for making the same.

2. Description of Related Art

Generally, a hygienic band comprises fluid permeable covering material, fluid impervious covering material, and a pad for absorbing secretion.

The fluid permeable covering material covers one side of the pad so that the pad cannot directly contact the skin of a user, thereby improving comfort. The impervious covering material covers the other side of the pad so that the absorbed secretion cannot flow to the user's clothing.

A hygienic band which is small in size while being able to absorb much secretion has been developed. A hygienic band having impervious covering material, which is thin while having an improved waterproof effect, has also been developed.

In recent years, a pad made of polymer having a high absorptive property has been used. In spite of the small size, this pad has high absorbtion strength.

However, when women are in menstruation, since the skin contacts the secretion for a long time, the contacted skin is apt to become infected.

SUMMARY OF THE INVENTION

Therefore, the present invention is made in an effort to solve the problems of the prior pad.

It is an object of the present invention to provide a pad which is hygienic when worn.

It is another object of the present invention to provide a pad which can be mass-produced.

To achieve the above objects, the present invention provides a pad comprising a face on which liquid mugwort or powder mugwort is spread or impregnated.

Alternatively, the present invention provides a pad comprising more than one sheet of mugwort-impregnated paper.

According to another aspect of the present invention, a method for making a mugwort-impregnated pad comprises the steps of:

breaking a lump of dry mugwort into 50-200 mesh size pieces;

straining the crushed mugwort to obtain mugwort naps without a stalk and chlorophyll;

fumigating the mugwort naps at a temperature of about 80°-130° for 1 or 2 hours;

diffusing the fumigated mugwort naps in water;

providing diffused mugwort naps to a refiner and mixing the naps with a lump of dissociated pulp;

preparing a sheet of paper by dehydrating the nap/pulp mixture; and attaching more than one sheet of paper on a pad.

According to another aspect of the present invention, a method for making a mugwort-impregnated pad comprises the steps of:

continuously transmitting a roll of pad above a reservoir containing a mugwort concentrate; and spreading the mugwort concentrate on the pad by contacting a roller, which is sunk into the mugwort concentrate and continuously rotated.

According to still another aspect of the present invention, a method for making a mugwort-impregnated pad, comprises the steps of:

transmitting a pad to an interior of a reservoir containing a mugwort concentrate;

impregnating the mugwort concentrate in the pad while the pad passes the interior of the reservoir; and transmitting the mugwort-impregnated pad to a drying system to dry the mugwort concentrate impregnated in the pad.

According to yet another aspect of the present invention, a method for making a mugwort-impregnated pad comprises the steps of:

transmitting a pad to an enclosed space isolated from an atmosphere; and spraying mugwort concentrate powder on the pad by using compressed air within the space. Preferably, the method further comprises the step of spreading binder on the pad before spraying mugwort concentrate powder on the pad.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein:

FIG. 5 is a schematic view illustrating a method for making a mugwort impregnated pad in accordance with a fourth embodiment of the present invention.

DETAILED DESCRIPTION OF THE PREFERRED EMBODIMENT

According to chinese medicine, mugwort is well known as a herb which is good for stopping bleeding, refining of blood, treating cuts and abrasions, alleviating pain and inflammation, and getting rid of bad odors.

For this reason, when mugwort is applied to a pad for women, the problems that appear in the prior art can be solved.

Figure 1:
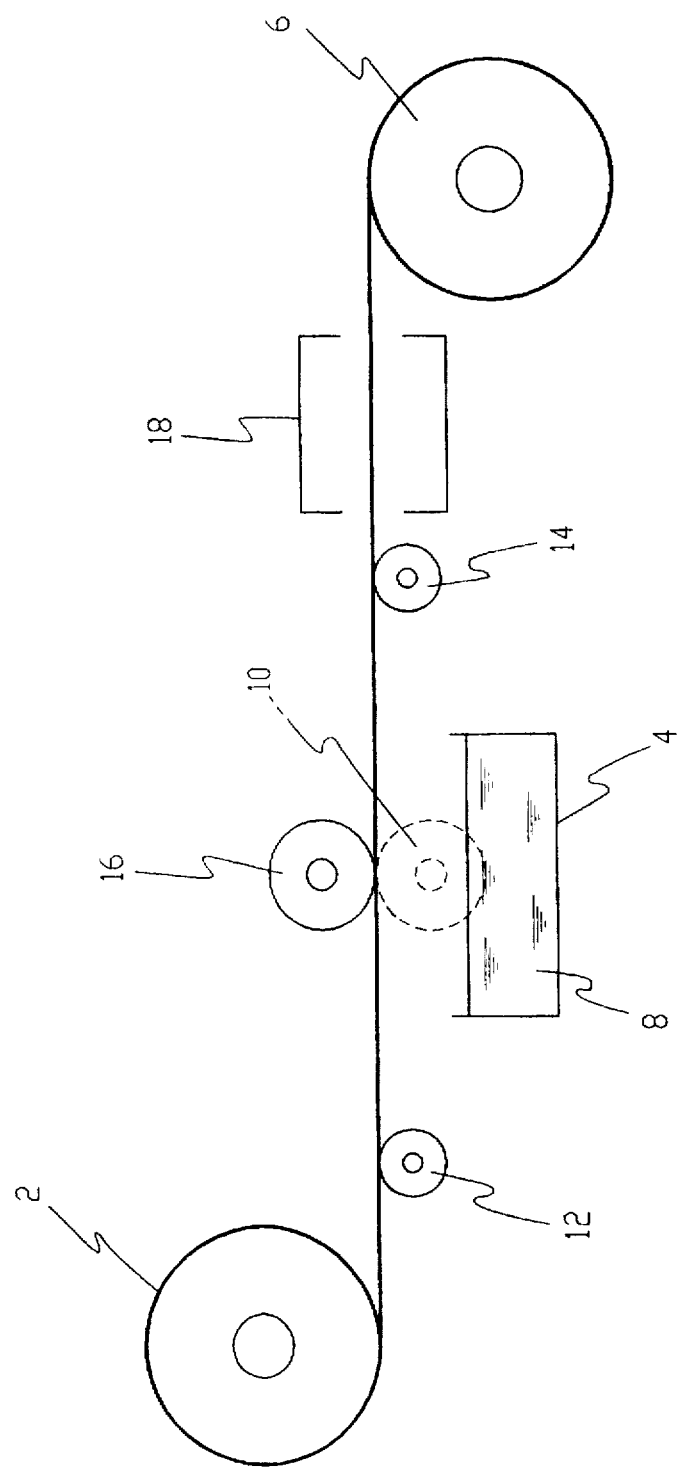
FIG. 1 is a schematic view illustrating a method for making a mugwort-impregnated pad in accordance with a first embodiment of the present invention.

FIG. 1 illustrates a method for making a pad where a mugwort concentrate is applied in accordance with a first embodiment of the present invention. A roll of strip-shaped pad 2 is released, passing through a reservoir 4 containing mugwort concentration, and is then re-rolled as a roll of mugwort-impregnated pad 6.

The mugwort concentrate 8 contained in the reservoir 4 is stained on a surface of a transition roller 10, a portion which is sunk into the mugwort concentrate, and is then absorbed on the pad passing through the roller 10. This will be described in more detail hereinbelow.

The mugwort concentrate 8 according to the present invention is obtained as follows. First, a lump of thoroughly dried mugwort is soaked in water for about 24 hours and is then transferred to a press system to press the juice out of the mugwort. Finally, this mugwort juice is strained through a 50–200 mesh sieve.

Preferably, the roller 10 is a sieve roller, on the surface of which a plurality of grooves are formed in a predetermined pattern so that the mugwort juice can be regularly fed to the pad.

The roll of strip-shaped pad 2 is guided by guide rollers 12 and 14, which are respectively arranged at front and rear sides of the transition roller 10, towards a position where this pad contacts the transition roller 10. A press roller 16 is disposed to be opposite to the transition roller 10 so that the pad can contact the transition roller 10 under sufficient pressure.

The pad applied with the mugwort juice 8 while contacting the transition roller 10 is transferred to a drying device 18.

The pad 2 is exposed to heat in the drying device 18 so that the mugwort juice can be dried, thereby obtaining a mugwort-impregnated pad 6.

Figure 2:
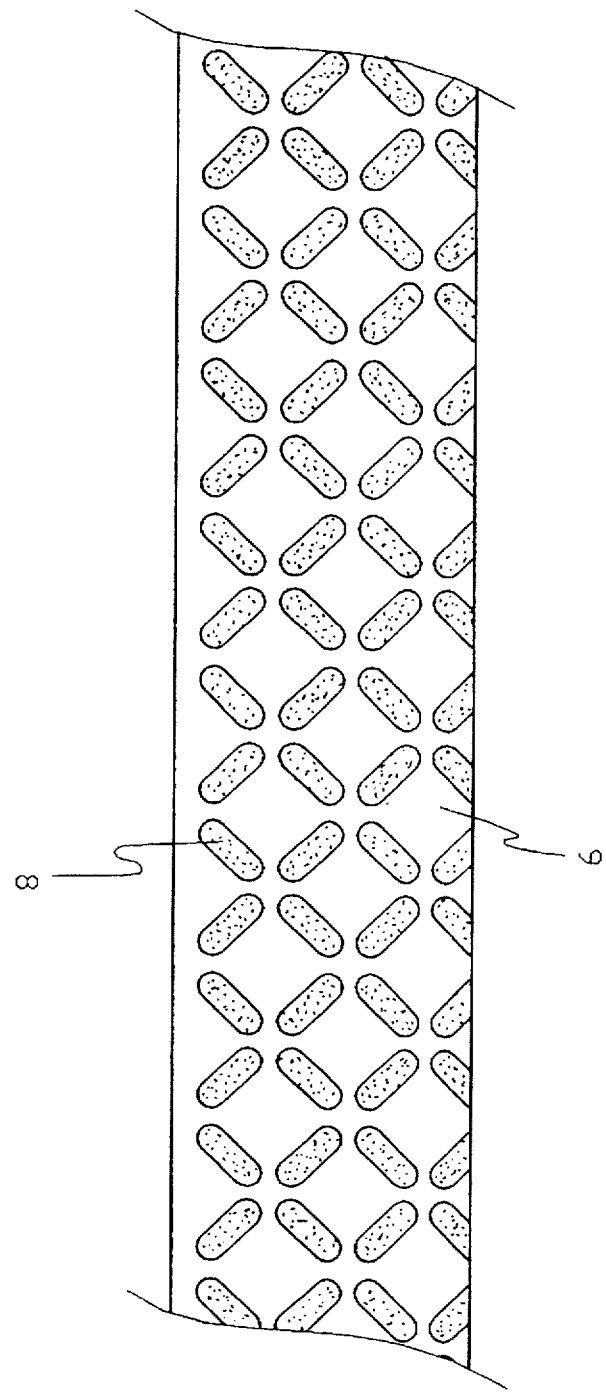
FIG. 2 is a view for showing a pad according to a preferred embodiment of the present invention.

FIG. 2 shows the mugwort-impregnated pad 6, wherein the dried mugwort 8 is applied on the pad 2 in a regular pattern.

The pad 6 made by the above described method is covered with a permeable material on one of its surfaces and with an impervious material on its other surface.

Figure 3:
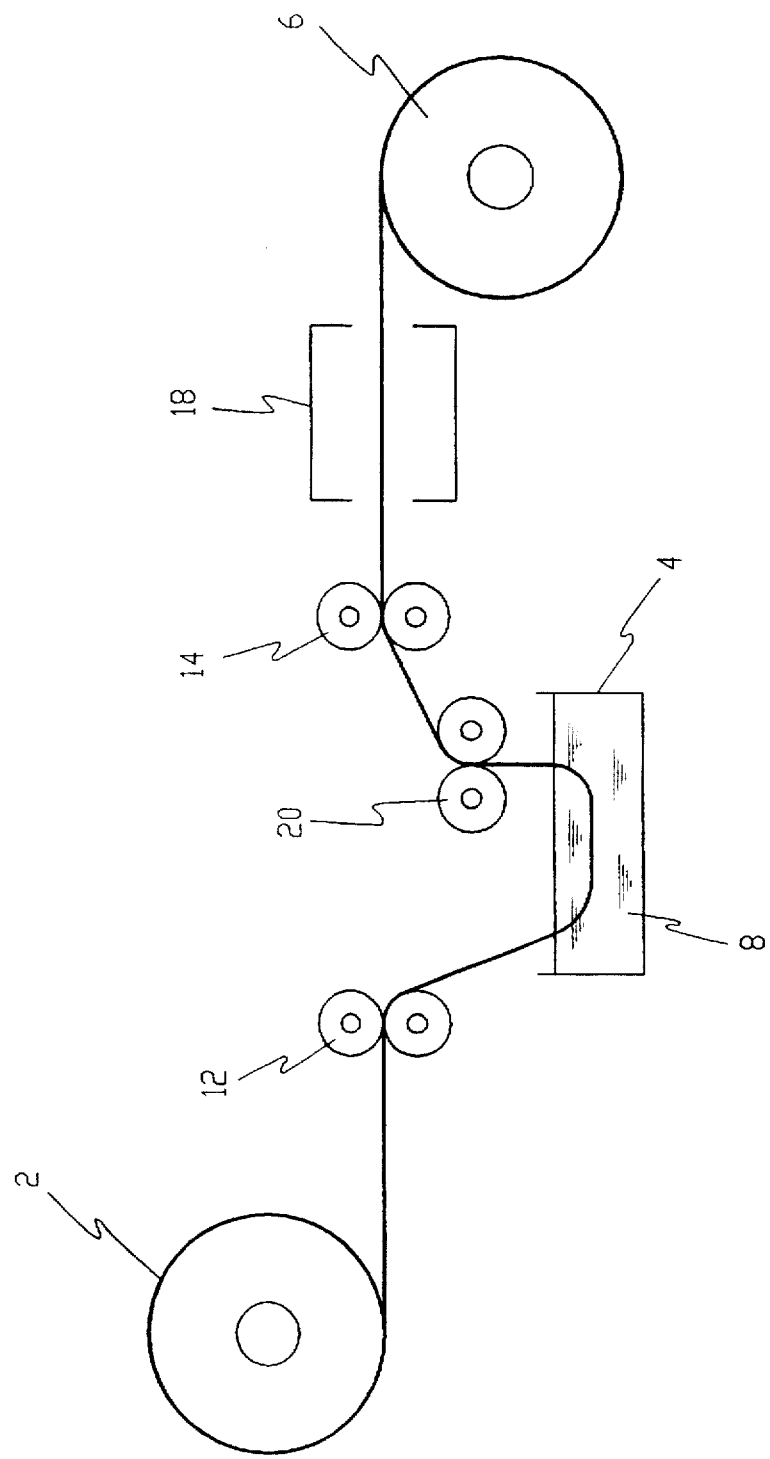
FIG. 3 is a schematic view illustrating a method for making a mugwort-impregnated pad in accordance with a second embodiment of the present invention.

FIG. 3 illustrates a method for making a mugwort-impregnated pad in accordance with a second embodiment of the present invention.

According to this embodiment, the pad is continuously fed to the reservoir 4 containing mugwort juice so that this mugwort juice can be directly absorbed into the pad 6.

The pad 2 passing through the mugwort juice 8 is transferred to a squeeze roller 20 so that mugwort juice excessively absorbed into the pad 2 can be squeezed out.

The pad 2 passing through the squeeze roller 20 is transferred to the drying device 18 so as to be dried therein and is then re-rolled as the mugwort-impregnated pad 6.

Although the time for drying the mugwort juice is prolonged, this embodiment has an advantage that the mugwort juice can be uniformly impregnated in the pad 2.

Figure 4:
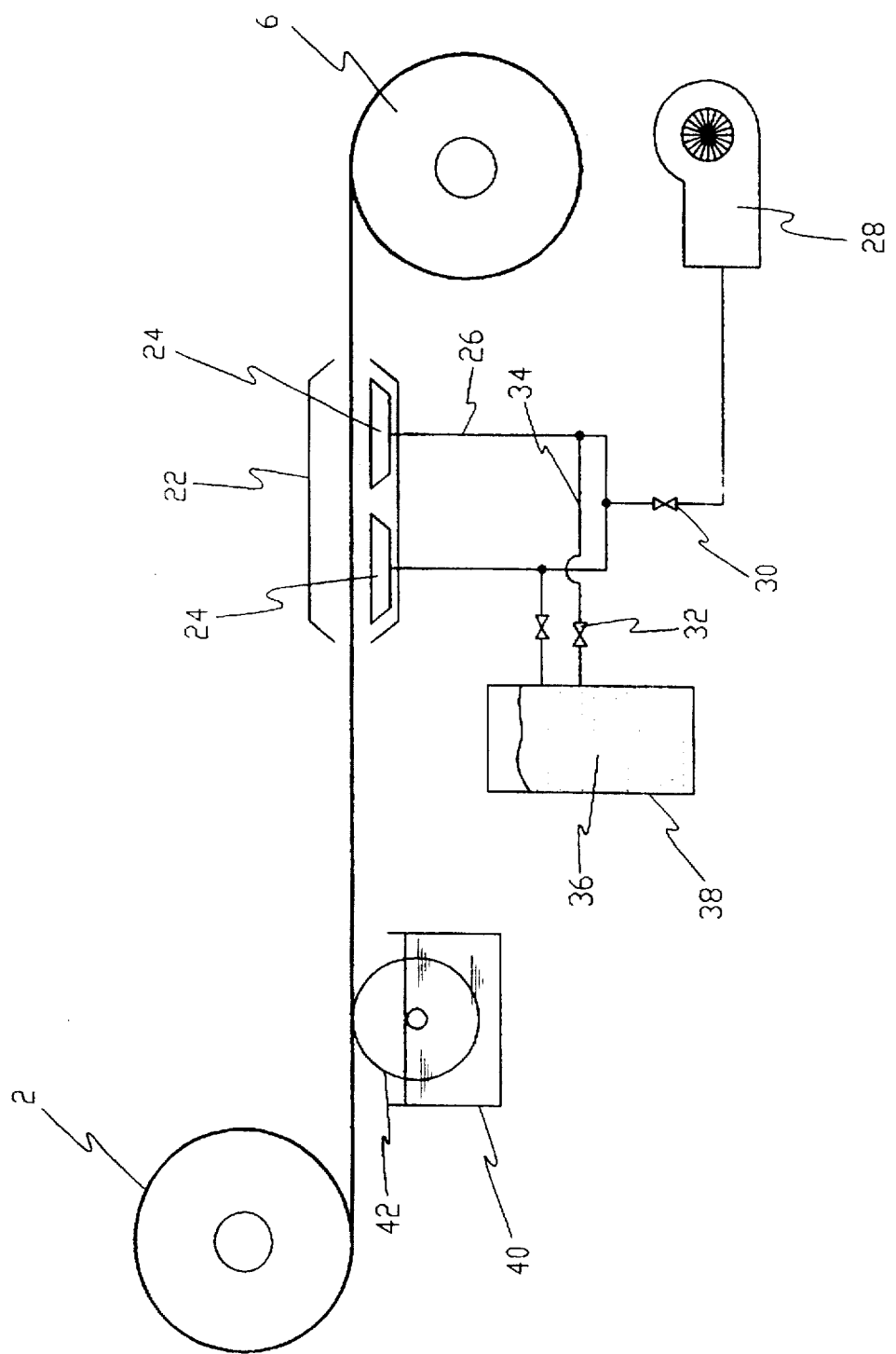
FIG. 4 is a schematic view illustrating a method for making a mugwort impregnated pad in accordance with a third embodiment of the present invention.

FIG. 4 illustrates a method for making a mugwort-impregnated pad in accordance with a third embodiment of the present invention.

In this embodiment, the pad 2 becomes the mugwort-impregnated pad 6 while passing through a confined space 22.

In the space 22, a plurality of diffusion plates 24 are arranged toward the lower face of the pad 2. The diffusion plate communicates with a compressor 28 through conduits 26. The communication between the diffusion plates 24 and the compressor 28 is controlled by a valve 30. A conduit 26 is branched off from the conduit 26, mounting a gate valve 32.

The conduit 34 extends from a reservoir 38 containing mugwort concentrate powder 36.

The mugwort concentrate powder 36 may be obtained by drying mugwort juice 8 in a vacuum drying manner.

In this embodiment, the pad 2 stays within the space 22 for a predetermined time. When the pad stays within the space 22, the compressor 28 and the diffusion plates 24 communicate with each other by both the valve 30 and the gate valve 32 so that compressed air can be sprayed toward the pad 2 through the conduits 26.

During this process, since negative pressure is generated within the conduit 32, the mugwort concentrate powder 36 is carried by the compressed air, being sprayed to one face of the pad 2.

At this point, the mugwort concentrate powder 36 is impregnated by force of the compressed air.

If required, one face of the pad 2 may be provided with a binder to effectively attach the powder 36 on the face of the pad.

Preferably, the binder may be selected from inorganic material which is not harmful to persons. The binder may be spread on the face of the pad before this is transferred to the space 22. That is, a reservoir containing the binder is located on the front side of the space. The binder is spread on the pad while a roller rotates. A portion of the roller is sank to the binder within the reservoir 40.

When the inorganic binder is spread on the pad 2, the sprayed mugwort concentrate powder 36 can be easily attached on the face of the pad.

In addition, the pad according to the present invention can be made of more than one layer of mugwort sheet.

The mugwort sheet can be obtained through the following manner.

First, a lump of dry mugwort is crushed into 50–200 mesh size pieces and is then strained by a sieve to obtain a certain amount of mugwort naps. The mugwort naps are fumigated in a steam boiler having a temperature of about 80°–130°, preferably 100°, for 1 or 2 hours, preferably, 1 hour and 30 minutes. This fumigation process sterilizes the mugwort naps and, at the same time, balances the water content within the mugwort.

The fumigated mugwort naps are diffused in water contained in a tank used in a conventional paper manufacturing process.

The water content is dehydrated during the initial paper process.

In addition, the mugwort naps are mixed with a lump of dissociated pulp, which is dissociated in a conventional manner, and is then transferred to a refiner. The mixing rate of the mugwort naps to the pulp is preferably from 1:9 to 9:1.

The mixture can be a mugwort-impregnated sheet through the conventional paper manufacturing process.

The mugwort-impregnated sheet is applied to a conventional pad. The pad applied with mugwort-impregnated sheet is stitched while passing through a needle punching machine 22 as shown in FIG. 5, thereby obtaining a mugwort-impregnated pad.

What is claimed is:

1. A method for mass-producing hygienic bands containing mugwort concentrate, comprising the steps of:

continuously transmitting a roll of pad above a reservoir containing a mugwort concentrate; and spreading the mugwort concentrate on the pad by contacting a roller, which is sunk into the mugwort concentrate and continuously rotated.

2. A method according to claim 1 wherein said roller simultaneously advances said pad and applies said mugwort concentrate to said pad.

3. A method according to claim 1 wherein said roller is a sieve roller containing a plurality of contours formed in a predetermined pattern configured so as to evenly apply said mugwort concentrate to said pad as said pad contacts said sieve roller.

4. A method according to claim 1 further comprising the step of applying a force upon said pad at approximately the point of contact of said pad with said roller such that said pad maintains contact with said roller during said spreading step.

5. A method for mass-producing hygienic bands containing mugwort concentrate, comprising the steps of:

transmitting a pad to an interior of a reservoir containing a mugwort concentrate;

impregnating the mugwort concentrate in the pad while the pad passes the interior of the reservoir; and transmitting the mugwort-impregnated pad to a dry system to dry the mugwort concentrate impregnated in the pad.

6. A method according to claim 5 further comprising the step of passing said pad through a squeeze roller after said impregnating step to remove excess mugwort concentrate absorbed in said pad.

7. A method according to claim 5 wherein said impregnation step uniformly impregnates said pad with said mugwort concentrate.

8. A method for mass-producing hygienic bands containing mugwort concentrate, comprising the steps of:

transmitting a pad to an enclosed space; and spraying mugwort concentrate powder on the pad by using compressed air within the space.

9. A method according to claim 8 further comprising the step of spreading binder on the pad before spraying mugwort concentrate powder on the pad.

10. A method according to claim 9 wherein said binder is a fluid applied to said pad by a roller partially immersed within a reservoir containing said fluid.

11. A method according to claim 8 further comprising the steps of:

drawing said powder from a reservoir with said compressed air; and conveying said powder and said compressed air through a conduit connected between said reservoir and said space.

12. A method according to claim 11 further comprising the step of opening a valve connecting said conduit to said compressed air.

13. A method according to claim 8 further comprising the steps of:

carrying said powder to a plurality of diffusion plates located within said enclosed space; and dispersing said powder out of said diffusion plates.

* * * * *